United States Patent
Wright et al.

(10) Patent No.: US 6,264,987 B1
(45) Date of Patent: Jul. 24, 2001

(54) METHOD FOR PREPARING MICROPARTICLES HAVING A SELECTED POLYMER MOLECULAR WEIGHT

(75) Inventors: Steven G. Wright, Madeira; Michael E. Rickey, Loveland; J. Michael Ramstack, Lebanon; Shawn L. Lyons; Joyce M. Hotz, both of Cincinnati, all of OH (US)

(73) Assignee: Alkermes Controlled Therapeutics Inc. II, Cambridge, MA (US)

( * ) Notice: Subject to any disclaimer, the term of this patent is extended or adjusted under 35 U.S.C. 154(b) by 0 days.

(21) Appl. No.: 09/575,075

(22) Filed: May 19, 2000

(51) Int. Cl.[7] ................ A61K 9/14; A61K 9/50; B01J 13/02
(52) U.S. Cl. .............. 424/489; 424/497; 424/484; 264/41; 264/46; 427/213.3; 427/213.36
(58) Field of Search ................. 424/489, 497; 264/41, 46; 427/213.3, 213.36

(56) References Cited

U.S. PATENT DOCUMENTS 5,654,008 * 8/1997 Herbert et al. .................. 424/489

* cited by examiner

Primary Examiner—Thurman K. Page
Assistant Examiner—Blessing Fubara
(74) Attorney, Agent, or Firm—Andrea G. Reister; Covington & Burling

(57) ABSTRACT

A method for preparing microparticles having a selected polymer molecular weight. The hold time and temperature of a solution containing a nucleophilic compound and a polymer having a starting molecular weight are controlled in order to control the molecular weight of the polymer in the finished microparticle product. In this manner, a selected polymer molecular weight in the finished microparticle product can be achieved from a variety of starting material molecular weights.

50 Claims, 4 Drawing Sheets

METHOD FOR PREPARING MICROPARTICLES HAVING A SELECTED POLYMER MOLECULAR WEIGHT

BACKGROUND OF THE INVENTION

1. Field of the Invention

The present invention relates to preparation of microparticles. More particularly, the present invention relates to a method and an apparatus for preparing microparticles having a selected polymer molecular weight.

2. Related Art

A variety of methods is known by which compounds can be encapsulated in the form of microparticles. It is particularly advantageous to encapsulate a biologically active or pharmaceutically active agent within a biocompatible, biodegradable wall forming material (e.g., a polymer) to provide sustained or delayed release of drugs or other active agents. In these methods, the material to be encapsulated (drugs or other active agents) is generally dissolved, dispersed, or emulsified, using stirrers, agitators, or other dynamic mixing techniques, in one or more solvents containing the wall forming material. Solvent is then removed from the microparticles and thereafter the microparticle product is obtained.

One variable that affects the in vitro and in vivo performance of the microparticle product is the molecular weight of the polymer or polymeric matrix material in the final microparticle product. Molecular weight affects drug release characteristics. The molecular weight of a polymer influences the biodegradation rate of the polymer. For a diffusional mechanism of active agent release, the polymer should remain intact until all of the active agent is released from the microparticles, and then degrade. The active agent can also be released from the microparticles as the polymeric matrix material bioerodes. By an appropriate selection of polymeric materials a microparticle formulation can be made in which the resulting microparticles exhibit both diffusional release and biodegradation release properties. This is useful in affording multiphasic release patterns.

It has been reported that the molecular weight of the poly(D,L-lactide) ("DL-PL") component of microcapsules containing up to 50% thioridazine free base decreased during fabrication, and in dissolution rate studies of the microcapsule (see Maulding, H.V. et al., Biodegradable Microcapsules: "Acceleration of Polymeric Excipient Hydrolytic Rate by Incorporation of a Basic Medicament", Journal of Controlled Release, Volume 3, 1986, pages 103–117; hereinafter "the Maulding article"). The results reported in the Maulding article reveal that the degradation rate of DL-PL in ketotifen free base microcapsules was greater when the encapsulation process was carried out at 4° C. than it was when the encapsulation process was carried out at 25° C. In contrast, the degradation rate of DL-PL in thioridazine free base microcapsules was greater when the encapsulation process was carried out at 23° C. than it was when the encapsulation process is carried out at 4° C. Based on these results, the Maulding article suggests circumventing the polymer degradation by carrying out the preparation of microcapsules at 4° C. in the case of thioridazine base. The Maulding article does not provide a method by which the molecular weight of the polymer in the finished microparticle can be conveniently controlled. Nor does the Maulding article provide a method for preparing microparticles that have a selected polymer molecular weight in the finished microparticle product.

Thus, there is a need in the art for an improved method for preparing microparticles that controls the molecular weight of the polymer or polymeric matrix material in the finished microparticle product. There is a particular need in the art for an improved process that provides a method for preparing microparticles that have a selected polymer molecular weight. The present invention, the description of which is fully set forth below, solves the need in the art for such an improved method.

SUMMARY OF THE INVENTION

The present invention relates to a method for preparing microparticles. The present invention allows microparticle products of varying polymer molecular weights to be produced using the same molecular weight starting material. The present invention also allows microparticle products with substantially the same polymer molecular weight to be produced from starting materials of varying molecular weight. In one aspect of the invention, a method of preparing microparticles having a selected microparticle polymer molecular weight is provided. The method comprises:

(a) preparing a first phase, the first phase comprising a nucleophilic compound, a polymer having a starting molecular weight, and a solvent for the polymer;

(b) combining the first phase with a second phase under the influence of mixing means to form an emulsion;

(c) combining the emulsion and an extraction medium, thereby forming microparticles; and (d) maintaining the first phase at a hold temperature for a hold period prior to step (b), the hold period of sufficient duration to allow the starting molecular weight of the polymer to reduce so that the selected microparticle polymer molecular weight is achieved.

In a further aspect of the present invention, another method for preparing microparticles is provided. The method comprises:

(a) providing a polymer having a starting molecular weight;

(b) dissolving the polymer and a nucleophilic compound in a solvent to form a first phase;

(c) combining the first phase with a second phase under the influence of mixing means to form an emulsion;

(d) combining the emulsion and an extraction medium, thereby forming microparticles; and (e) maintaining the first phase at a hold temperature for a hold period prior to step (c), wherein the hold period is selected so that the starting molecular weight reduces so that a selected microparticle polymer molecular weight is achieved.

In other aspects of the present invention, the foregoing methods comprise adding an active agent to the first phase. In yet further aspects of the present invention, the foregoing methods comprise adding an inactive agent to the first phase.

In further aspects of the invention, the hold temperature is increased, thereby increasing the molecular weight decay of the polymer to reduce the duration of the hold period. The hold temperature can be decreased, thereby decreasing the molecular weight decay of the polymer to increase the duration of the hold period.

Other aspects of the present invention include a microencapsulated active agent and microparticles prepared by the methods of the present invention.

Features and Advantages

It is a feature of the present invention that it can be used to prepare microparticles, including microparticles containing an active agent.

It is a further feature of the present invention that it allows the hold time and temperature of a nucleophilic compound/ polymer solution to be modified to achieve a selected polymer molecular weight in the microparticle product.

An advantage of the present invention is that a selected polymer molecular weight can be achieved in the microparticle product by using a variety of polymers, having varying starting molecular weights, by varying the hold time of the nucleophilic compound/polymer solution.

A further advantage of the present invention is that microparticle products of varying polymer molecular weights can be produced using the same starting polymer, or using a polymer having the same starting molecular weight.

BRIEF DESCRIPTION OF THE DRAWINGS

The present invention is described with reference to the accompanying drawings. In the drawings, like reference numbers indicate identical or functionally similar elements.

DETAILED DESCRIPTION OF THE DRAWINGS

Overview

Figure 1:
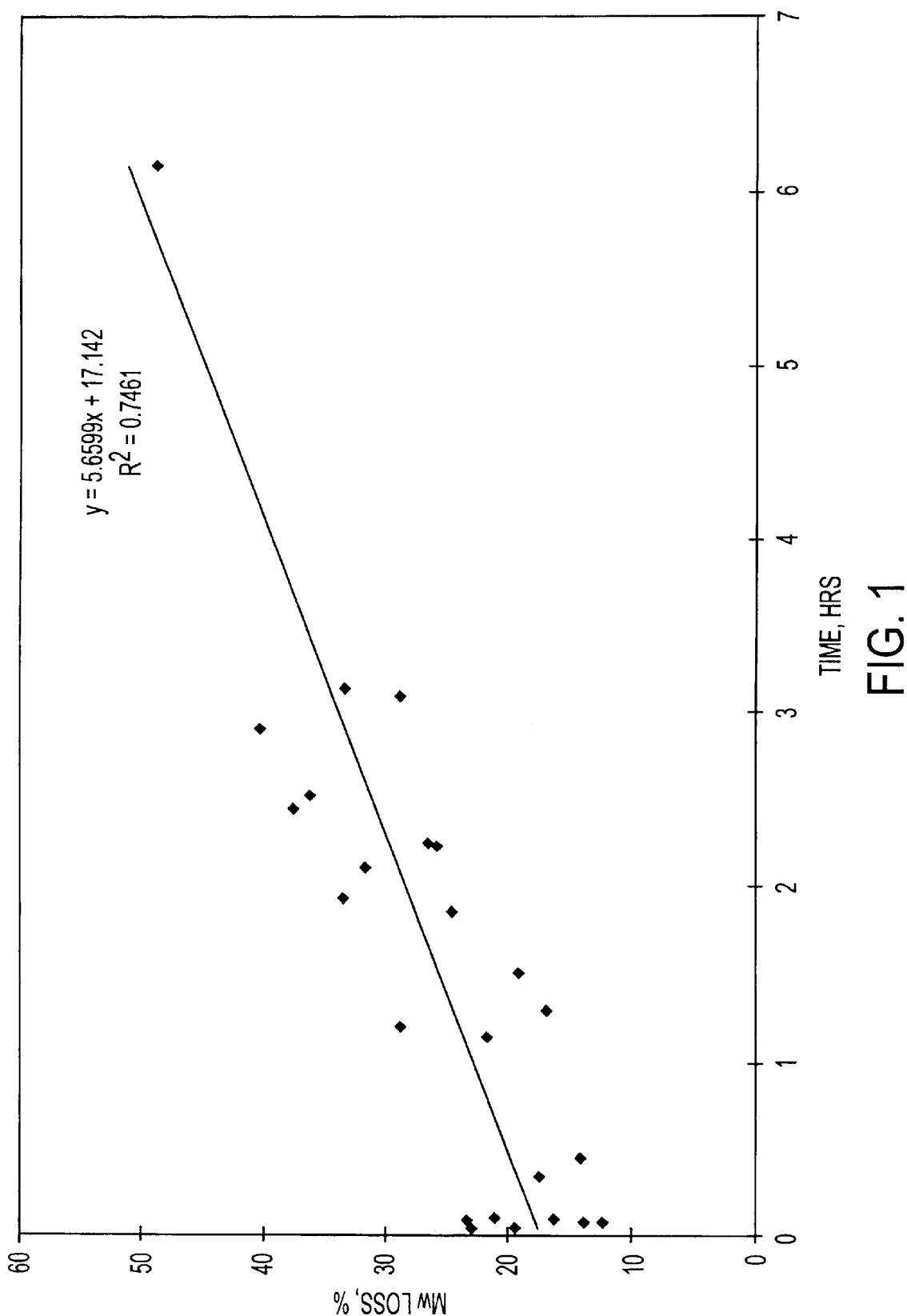
FIG. 1 depicts a graph of molecular weight loss percentage as a function of solution hold time (hours) at a 1 kg scale.

The present invention provides an improved method for preparing microparticles. The methods of the present invention control the hold time and temperature of a polymer solution in order to control the molecular weight of the polymer in the finished microparticle product. In this manner, the methods of the present invention advantageously allow a selected polymer molecular weight to be achieved from a variety of starting material molecular weights. Alternatively, microparticle products of varying polymer molecular weights can be produced using the same molecular weight starting material. Thus, a range of products can be made from the same starting materials, thereby eliminating the need to reformulate the finished product to achieve the desired molecular weight of the polymer in the finished product.

The polymer solution used in the present invention comprises a nucleophilic compound. As used herein, "nucleophilic compound" refers to a compound that promotes by nucleophilic catalysis the ester hydrolysis, such as the polymer scission, that occurs in the biodegradation of biodegradable polymers, such as polymers comprising varying lacotide:glycolide ratios. A nucleophilic compound is a more effective nucleophile toward an ester group of the polymer than hydroxide ion or water. Nucleophilic compounds that catalyze the polymer hydrolysis include, but are not limited to, amines and carboxylate anions, and can be "active agents" (defined below) or "inactive agents" that are not active agents. Examples of nucleophilic compounds that are active agents include, but are not limited to, risperidone, 9-hydroxyrisperidone, and pharmaceutically acceptable salts of the foregoing, naltrexone, and oxybutynin. Examples of nucleophilic compounds that are inactive agents include, but are not limited to, protamine sulfate, spermine, choline, ethanolamine, diethanolamine, and triethanolamine. It should be readily apparent to be one skilled in the art that the present invention is not limited to any particular nucleophilic compound, and that the present invention encompasses other nucleophilic active agents and nucleophilic inactive agents.

To ensure clarity of the description that follows, the following definitions are provided. By "microparticles" or "microspheres" is meant particles that comprise a polymer that serves as a matrix or binder of the particle. The microparticle may contain an active agent or other substance dispersed or dissolved within the polymeric matrix. The polymer is preferably biodegradable and biocompatible. By "biodegradable" is meant a material that should degrade by bodily processes to products readily disposable by the body and should not accumulate in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body. By "weight %" or "% by weight" is meant parts by weight per total weight of microparticle. For example, 10 wt. % active agent would mean 10 parts active agent by weight and 90 parts polymer by weight. By "controlled release microparticle" or "sustained release microparticle" is meant a microparticle from which an active agent or other type of substance is released as a function of time. By "mass median diameter" is meant the diameter at which half of the distribution (volume percent) has a larger diameter and half has a smaller diameter.

By "active agent" is meant an agent, drug, compound, composition of matter or mixture thereof which provides some pharmacologic, often beneficial, effect. This includes foods, food supplements, nutrients, drugs, vitamins, and other beneficial agents. As used herein, the terms further include any physiologically and pharmacologically active substance that produces a localized or systemic effect in a patient. Such active agents include antibiotics, antiviral agents, anepileptics, analgesics, anti-asthmatics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, leukotriene antagonists, antiparasites, neoplastics, antineoplastics, hypoglycemics, nutritional agents and supplements, growth supplements, fats, ophthalmics, antienteritis agents, electrolytes and diagnostic agents.

Method and Examples

The following examples are provided to explain the invention, and to describe the materials and methods used in carrying out the invention. The examples are not intended to limit the invention in any manner.

Molecular Weight Experiments with Nucleophilic Compounds

EXAMPLE 1

A series of experiments were conducted at the 1 kg scale that demonstrate the relationship between molecular weight of the finished microparticle product, and the duration of a hold period of a nucleophilic compound/polymer solution. Microparticles comprising risperidone were prepared at the one-kilogram scale. The 1 Kg process (400 grams of active agent and 600 grams of polymer) provides a theoretical drug loading of the microparticles of 40% (400 grams/1000 grams×100%).

A 16.7 wt. % polymer solution was prepared by dissolving 600 grams of MEDISORB® 7525 DL polymer (Alkermes, Inc., Blue Ash, Ohio) in ethyl acetate. A 24 wt. % drug solution was prepared by dissolving 400 grams of risperidone (basic nucleophilic active agent) (Janssen Pharmaceutica, Beerse, Belgium) in benzyl alcohol. A nucleophilic active agent/polymer solution (organic phase) was prepared by mixing the drug solution into the polymer solution. The active agent/polymer solution was maintained at a temperature of 25±5° C. The active agent/polymer solution is held for a hold time of sufficient duration to achieve the selected or desired polymer molecular weight in the finished microparticle product, based on the starting molecular weight of the polymer. The results of the experiments, showing the effect of hold time on molecular weight loss, are discussed in more detail below with respect to Table 1 and FIG. 1.

The second, continuous phase was prepared by preparing a 30 liter solution of 1% polyvinyl alcohol (PVA), the PVA acting as an emulsifier. To this was added 2086 grams of ethyl acetate to form a 6.5 wt. % solution of ethyl acetate. The two phases were combined using a static mixer, such as a ½" Kenics static mixer available from Chemineer, Inc., North Andover, Mass. A total flow rate of 3 L/min generally provides microparticle size distributions with a mass median diameter (MMD) in the range of about 80–90$\mu$. The ratio of continuous phase to discontinuous phase was 5:1 (v/v).

The quench liquid was 2.5% solution of ethyl acetate and water-for-injection (WFI) at 5–10° C. The volume of the quench liquid is 0.25L per gram of batch size. The quench step was carried out for a time period greater than about 4 hours, with stirring of the microparticles in the quench tank.

After completion of the quench step, the microparticles were collected, de-watered, and dried. The temperature was maintained at less than about 15° C.

The microparticles were then re-slurried in a re-slurry tank using a 25% ethanol solution. The temperature in the re-slurry tank was in the range of about 0° C. to about 15° C. The microparticles were then transferred back to the quench tank for washing for a time period of at least 6 hours with another extraction medium (25% ethanol solution) that was maintained at preferably 25°±1° C.

The microparticles were collected, de-watered, and dried. The temperature was warmed to greater than about 20° C. but below 40° C. Drying continued for a time period greater than about 16 hours.

Twenty-four batches of risperidone microparticles at the 1 kg scale were prepared using the process described above. Table 1 below shows, for each batch, the starting molecular weight of the polymer (kD), the final molecular weight of the polymer in the finished microparticle product (kD), the percent loss in molecular weight of the polymer, and the hold time (hours) of the active agent/polymer solution. The molecular weight of the polymer in the finished microparticle product was determined by GPC.

TABLE 1

| Batch# | Starting Mw kD | Final Mw kD | % Loss | Hold time Hours |
|---|---|---|---|---|
| 825 | 230 | 182 | 21.0 | 0.10 |
| 708 | 161 | 110 | 32.0 | 2.08 |
| 714 | 161 | 133 | 17.3 | 0.33 |
| 812 | 161 | 100 | 37.9 | 2.40 |
| 819 | 161 | 102 | 36.7 | 2.47 |
| 319 | 131 | 110 | 16.2 | 0.10 |
| 331 | 131 | 115 | 12.2 | 0.07 |
| 423 | 131 | 78 | 40.7 | 2.85 |
| 506 | 129 | 112 | 13.6 | 0.07 |
| 512 | 129 | 86 | 33.7 | 3.10 |
| 520 | 129 | 92 | 29.1 | 3.07 |
| 527 | 129 | 95 | 26.8 | 2.22 |
| 603 | 129 | 65 | 49.4 | 6.10 |
| 610 | 129 | 101 | 22.0 | 1.13 |
| 617 | 128 | 95 | 26.1 | 2.20 |
| 902 | 128 | 85 | 33.8 | 1.90 |
| 908 | 128 | 91 | 29.0 | 1.18 |
| 921 | 128 | 99 | 23.2 | 0.08 |
| 930 | 128 | 103 | 19.4 | 0.03 |
| 915 | 92 | 69 | 24.8 | 1.82 |
| 1021 | 135 | 104 | 23.0 | 0.03 |
| 1028 | 138 | 119 | 13.7 | 0.45 |
| 1110 | 138 | 115 | 16.8 | 1.28 |
| 1215 | 138 | 111 | 19.4 | 1.50 |

The data reported in Table 1 is depicted in the graph shown in FIG. 1. FIG. 1 shows an initial loss in molecular weight of approximately 17%, with an additional loss of approxamately 5.7% per hour of hold time of the active agent/polymer solution.

EXAMPLE 2

Additional experiments were conducted at the 20 kg scale that also demonstrate the relationship between molecular weight of the finished microparticle product, and the duration of a hold period of a nucleophilic compound/polymer solution. Microparticles comprising risperidone were prepared at the twenty-kilogram scale. The 20 Kg process (8 kg of active agent and 12 kg of polymer) provides a theoretical drug loading of the microparticles of 40% (8 kg/20 kg×100%).

A 16.7 wt. % polymer solution was prepared by dissolving 12 kg of MEDISORB® 7525 DL polymer (Alkermes, Inc., Blue Ash, Ohio) in ethyl acetate. A 24 wt. % drug solution was prepared by dissolving 8 kg of risperidone (Janssen Pharmaceutica, Beerse, Belgium) in benzyl alcohol. A nucleophilic active agent/polymer solution (organic phase) was prepared by mixing the drug solution into the polymer solution. The active agent/polymer solution was maintained at a temperature of 25±5° C. The active agent/polymer solution is held for a hold time of sufficient duration to achieve the selected or desired polymer molecular weight in the finished microparticle product, based on the starting molecular weight of the polymer. The results of the experiments, showing the effect of hold time on molecular weight loss, are discussed in more detail below with respect to Table 2 and FIG. 2.

The second, continuous phase was prepared by preparing a 600 liter solution of 1% PVA, the PVA acting as an emulsifier. To this was added 42 kg of ethyl acetate to form a 6.5 wt. % solution of ethyl acetate. The two phases were combined using a static mixer, such as a 1" Kenics static mixer available from Chemineer, Inc., North Andover, Mass.

The quench liquid was 2.5% solution of ethyl acetate and water-for-injection (WFI) at 5–10° C. The volume of the quench liquid is 0.25L per gram of batch size. The quench step was carried out for a time period greater than about 4 hours, with stirring of the microparticles in the quench tank.

After completion of the quench step, the microparticles were collected, de-watered, and dried. The temperature was maintained at less than about 15° C.

The microparticles were then re-slurried in a re-slurry tank using a 25% ethanol solution. The temperature in the re-slurry tank was in the range of about 0° C. to about 15% microparticles were then transferred back to the quench tank for washing for a time period of at least 6 hours with another extraction medium (25% ethanol solution) that was maintained at preferably 25°±1° C.

The microparticles were collected, de-watered, and dried. The temperature was greater than about 20° C. but below 40° C. Drying continued for a time period about 16 hours.

Four batches of risperidone microparticles at the 20 kg scale were prepared using the process described above. Table 2 below shows, for each batch, the starting molecular wieght of the polymer (kD), the final molecular weight of the polymer in the finished microparticle product (kD), the percent loss in molecular weight of the polymer, and the hold time hours) of the active agent/polymer solution. The molecular weight of the polymer in the finished microparticle product was determined by GPC.

TABLE 2

| Batch# | Starting Mw kD | Final Mw kD | % Loss | Hold time hours |
|---|---|---|---|---|
| 3308 | 146 | 117 | 20 | 0.5 |
| 4068 | 145 | 103 | 29 | 1.75 |
| 4138 | 143 | 111 | 22 | 1.0 |
| 4208 | 143 | 110 | 23 | 1.0 |

Figure 2:
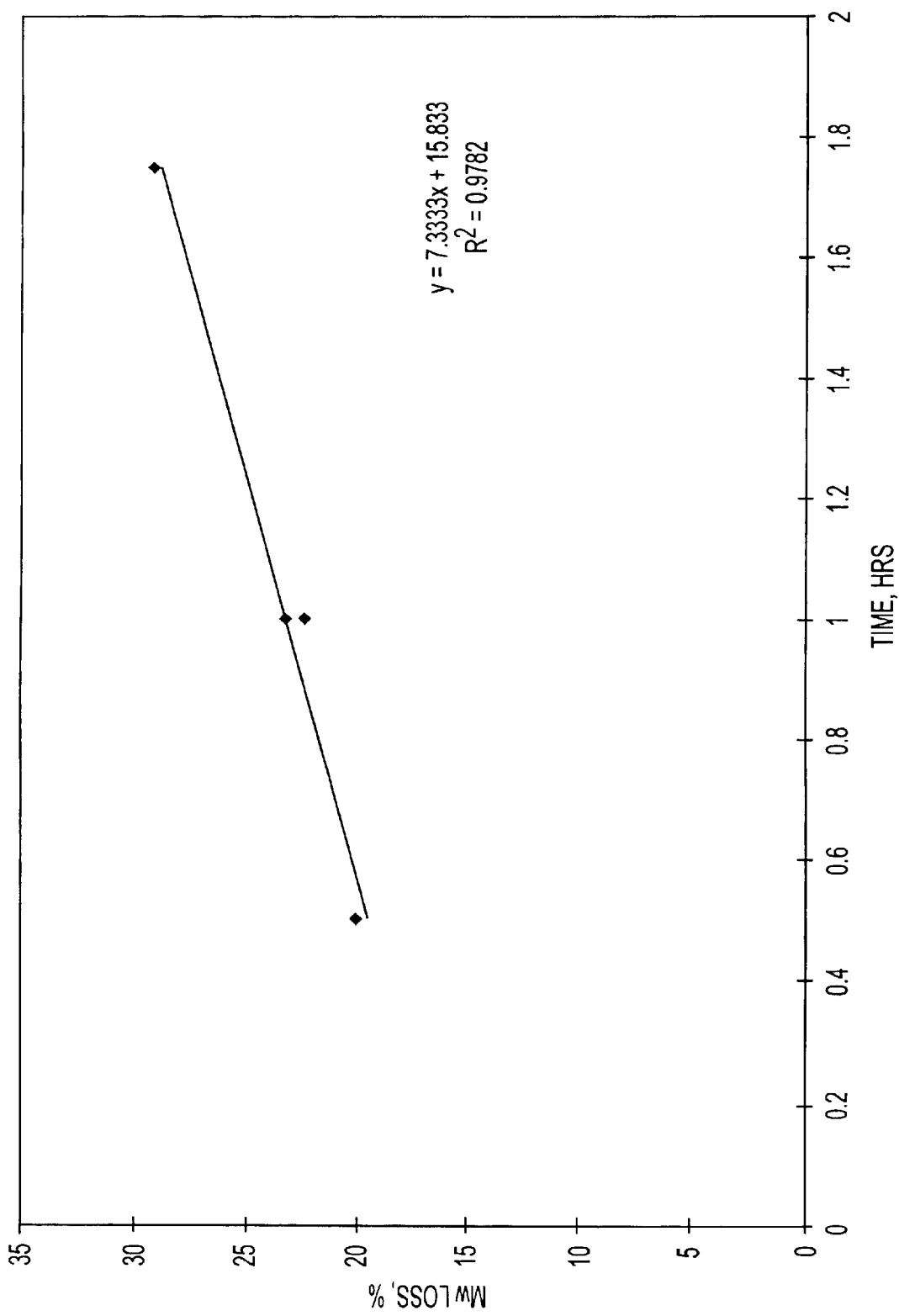
FIG. 2 depicts a graph of molecular weight loss percentage as a function of solution hold time (hours) at a 20 kg scale.

The data reported in Table 2 show that from a relatively constant molecular wieght starting material (143 kD, 145 kD, and 146 kD), a variable finished microparticle product molecular weight was achieved by varying the hold time of the active agent/polymer solution hold time. The data reported in Table 2 is depicted in the graph shown in FIG. 2. FIG. 2 shows an initial loss in molecular weight of approximately 16%, with an additional loss of approximately 7.3% per hour of hold time of the active agent/polymer solution.

EXAMPLE 3

The starting molecular weight of the polymer (kD) and the final molecular weight of the polymer in a finished microparticle product (kD) was determined for microparticles containing the nucleophilic compound naltrexone. The starting polymer lactide:glycolide ratio was 75:25, 85:15, and 65:35. The polymers used were MEDISORB® 7525 DL polymer, MEDISORB® 8515 DL polymer and MEDISORB® 6535 DL polymer, all available from Alkermes, Inc., Blue Ash, Ohio.

The naltrexone base microparticles were produced using a co-solvent extraction process. The theoretical batch size was 15 to 20 grams. The polymer was dissolved in ethyl acetate to produce a 16.7% w/w polymer solution. The naltrexone base anhydrous was dissolved in benzyl alcohol to produce a 30.0% w/w solution. In various batches, the amount of drug and polymer used was varied to produce microparticles with different theoretical drug loading ranging from 30%–75%. The ambient polymer and drug solutions were mixed together until a single homogeneous solution (organic phase) was produced. The aqueous phase was at ambient conditions and contained 1% w/w polyvinyl alcohol and a saturating amount of ethyl acetate. These two solutions were pumped via positive displacement pumps at a ratio of 3:1 (aqueous:organic) through a ¼" in-line mixer to form an emulsion. The emulsion was transferred to a stirring solvent extraction solution consisting of 2.5% w/w of ethyl acetate dissolved in distilled water at 5–10° C. and at a volume of 0.5L of extraction solution per theoretical gram of microparticles. Both the polymer and drug solvents were extracted into the extraction solution from the emulsion droplets to produce microparticles. The initial extraction process ranged from two to four hours. The microparticles were collected on a 25 μm sieve and rinsed with a cold (<5° C.) 25% w/w ethanol solution. The microparticles were dried cold overnight (approximately 17 hours) using nitrogen. The microparticles were then transferred to the reslurry solution, which consisted of a vigorously stirring 25% w/w ethanol solution at 5–10° C. After a short mixing time (five to fiffteen minutes), the reslurry solution and the microparticles were transferred to a stirring 25% w/w ethanol secondary extraction solution (approximately 25° C. at a volume of 0.2 L of secondary extraction solution per theoretical gram of microparticles). The microparticles stirred for six hours enabling additional solvent removal from the microparticles to take place. The microparticles were then collected on a 25 μm sieve and rinsed with a 25% w/w ethanol solution at ambient temperature. These microparticles dried in a hood under ambient conditions overnight (approximately 17 hours), were sieved to remove agglomerated microparticles and then placed into a freezer for storage.

As shown below in Table 3, three batches of microparticles were prepared using the 75:25 polymer, two batches for the 85:15 polymer, and four batches for the 65:35 polymer. For each batch, Table 3 shows the starting molecular weight of the polymer (kD), and the final molecular weight of the polymer in the finished microparticle products (kD), and the percent loss in molecular weight of the polymer. The molecular weight of the polymer in the finished microparticle product was determined by GPC. The data in Table 3 provides an example of the loss in molecular weight of the polymer in a finished microparticle product containing a nucleophilic compound (naltrexone) for polymers having varying lactide:glycolide ratios.

TABLE 3

| Starting Polymer Lactide:glycolide ratio | Batch | Starting Mw kD | Final Mw kD | % Loss |
|---|---|---|---|---|
| 75:25 | 99-123-004 | 116.2 | 76.0 | 34.6 |
|  | 99-123-009 | 116.2 | 74.0 | 36.3 |
|  | 99-123-012 | 116.2 | 74.3 | 36.1 |
| 85:15 | 99-123-016 | 109.7 | 83.7 | 23.7 |
|  | 99-123-024 | 109.7 | 74.9 | 31.7 |
| 65:35 | 99-123-021 | 102.3 | 56.3 | 45.0 |
|  | 99-123-028 | 102.3 | 63.4 | 38.0 |
|  | 99-123-037 | 102.3 | 69.6 | 32.0 |
|  | 99-123-034 | 102.3 | 79.6 | 22.2 |

EXAMPLE 4

Additional experiments were conducted with other polymers that also demonstrate the relationship between molecular weight of the finished microparticle product, and the duration of a hold period of a nucleophilic compound/ polymer solution. Microparticles comprising other polymers having different lactide:glycolide ratios were prepared. Microparticles comprising risperidone using polymers having lactide:glycolide ratios of 65:35, 85:15, and 100:0 were prepared at the 1 Kg scale using the same process described above in Example 1. The polymers used were MEDISORB® 6535 DL polymer, MEDISORB® 8515 DL polymer, and MEDISORB® 100 DL polymer, all available from Alkermes, Inc., Blue Ash, Ohio.

Table 4 below shows, for each polymer, the starting molecular weight of the polymer (kD), the final molecular weight of the polymer in the finished microparticle product (kD), the percent loss in molecular weight of the polymer, and the hold time (hours) of the active agent/polymer solution. The molecular weight of the polymer in the finished microparticle product was determined by GPC.

TABLE 4

| Lactide:glycolide ratio | Starting Mw kD | Final Mw kD | % Loss | Hold time hours |
|---|---|---|---|---|
| 65:35 | 105 | 79 | 24.8 | 0.27 |
| 85:15 | 112 | 96 | 14.3 | 0.23 |
| 100 dl | 105 | 98 | 6.7 | 0.17 |

The data reported in Table 4 show that a microparticle product having about the same molecular weight (96 kD and 98 kD) can be prepared from two different molecular weight polymers (112 kD and 105 kD, respectively) having two different lactide:glycolide ratios (85:15 and 100:0, respectively). The present invention thus advantageously allows microparticle products with the same polymer molecular weight to be produced using two different starting materials.

EXAMPLE 5

Additional experiments were conducted that demonstrate the molecular weight loss of polymers in the presence of a nucleophilic compound (oxybutynin) as a function of time. Tests were conducted using a 100:0 lactide:glycolide polymer and two 75:25 lactide:glycolide polymers with differing inherent viscosity. For each test, the following protocol was carried out. Weigh about 6 g polymer into an Erlenmeyer flask. Add to the polymer 44 g ethyl acetate, sonicate and shake to dissolve the polymer. Weigh 1.5 g oxybutynin base. Stir the polymer solution, and add the drug to the polymer solution. Start the timer as the drug is added. Sample the drug/polymer solution at 1, 5 and 15 minutes, taking about ⅓ of the original volume for each aliquot as the solution stirs. Dispense the aliquot into 250 mL 50:50 H$_2$O:MeOH, and stir. This mix precipitates the polymer and removes the drug from the precipitate. Allow precipitated polymer to settle and decant the supernatant. Wash polymer residue with 100mL MeOH, stir approximately one minute, add up to 250 mL H$_2$O. Allow polymer to settle again, and repeat. Residue is then removed from the beaker and placed in a scintillation vial and frozen. Once all samples are collected and frozen, all samples are placed in a lyophilizer, cooled to −10° C. The lyophilizer is activated, and once a stable vacuum is achieved, the shelf temperature is raised to 15° C. and held overnight (~18 hours) to remove residual solvents.

The results of these experiments are shown in Table 5. For each experiment, the starting molecular weight of the polymer is shown, along with the polymer molecular weight at 1, 5, and 15 minutes of exposure of the polymer to the nucleophilic compound in the drug/polymer solution. As can be seen in Table 5, the longer the exposure or hold time of the drug/polymer solution, the lower the molecular weight of the polymer.

TABLE 5

| Starting Polymer Lactide:glycolide ratio | Starting Mw, kD | Time = 1 min Mw, kD | Time = 5 min Mw, kD | Time = 15 min Mw, kD |
|---|---|---|---|---|
| 100:0 | 77.1 | 67.2 | 63 | 60.8 |
| 75:25 | 82.8 | 56.2 | 55.1 | 48.8 |
| 75:25 | 54.1 | 44.1 | 42.9 | 38.4 |

Molecular Weight Temperature Experiments

EXAMPLE 6

Additional experiments were conducted to determine the effect of temperature on the relationship between molecular weight of the finished microparticle product, and the duration of a hold period of a nucleophilic compound/polymer solution. Fifty grams of risperidone (Janssen Pharmaceutica, Beerse, Belgium) were dissolved in 275 g of benzyl alcohol to form a drug solution. A polymer solution was formed by dissolving 75 g of MEDISORB® 7525 DL polymer (Alkerrnes, Inc., Blue Ash, Ohio) in ethyl acetate. The starting molecular weight of the polymer was 146 kD. The drug solution and the polymer solution were mixed to form a combined solution. A flask of the combined solution was placed in each of a 15° C., 25° C., and 35° C. chamber. At periodic time intervals, 10 cc of the combined solution was withdrawn from the flask in each chamber via a syringe and needle. The 10 cc sample was then precipitated in a bath containing 200 ml methanol at room temperature (approximately 20° C.). The polymeric precipitate was recovered from the methanol bath, and vacuum dried overnight. The dried samples were tested for their molecular weight by GPC.

Figure 3:
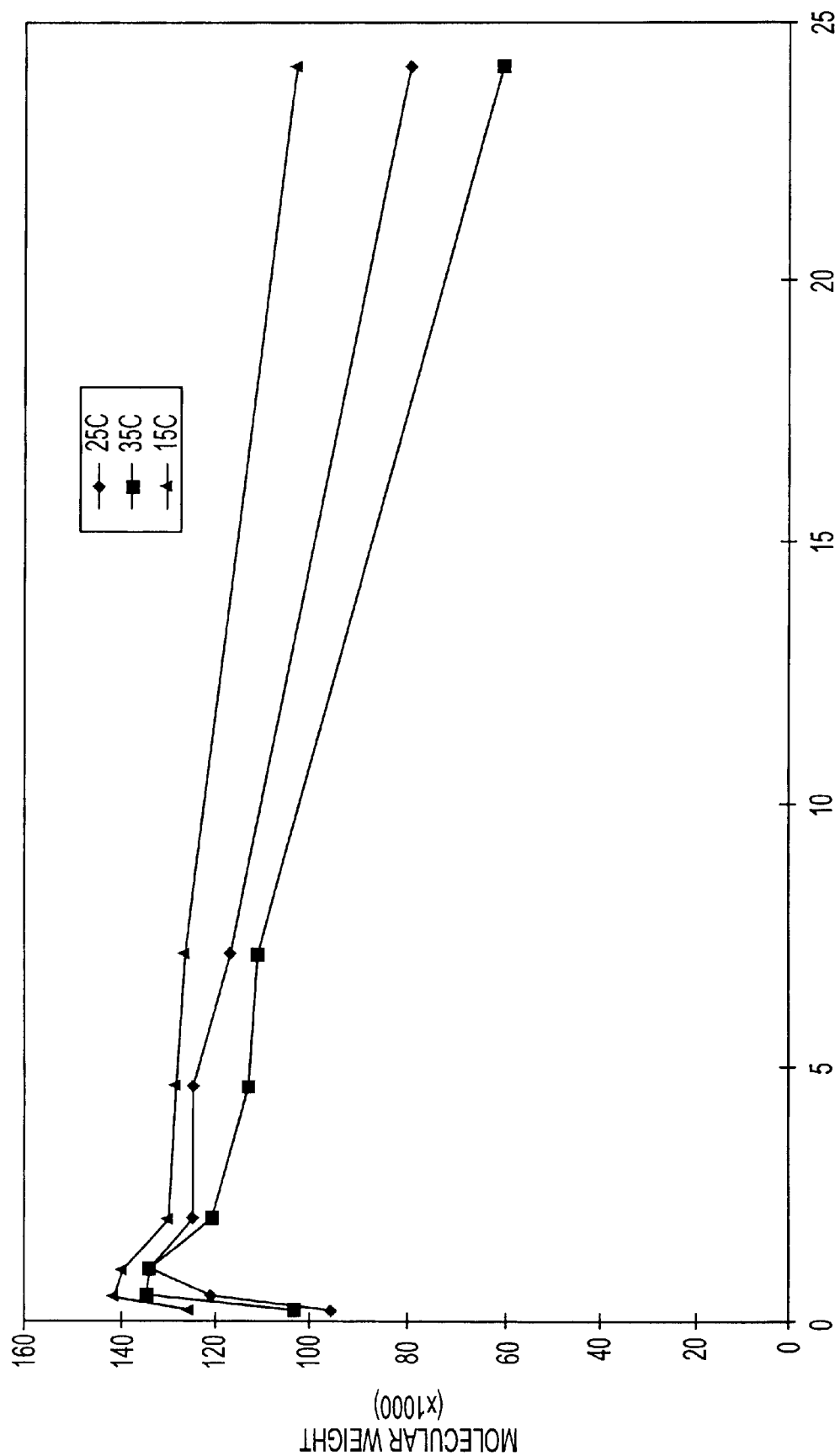
FIG. 3 depicts a graph of molecular weight (kD) as a function of solution hold time (hours) at 15° C., 25° C., and 35° C.

The results of the experiments are depicted in the graph of FIG. 3. As shown in FIG. 3, the molecular weight decay increases as temperature increases. Therefore, by increasing the hold temperature of the solution containing the polymer and the nucleophilic compound, the molecular weight decay of the polymer increases, and the duration of the hold period to achieve a particular molecular weight reduction is reduced. Similarly, by decreasing the hold temperature of the solution containing the polymer and the nucleophilic compound, the molecular weight decay of the polymer decreases, and the duration of the hold period to achieve a particular molecular weight reduction is increased. For example, the time required to reduce the molecular weight form 130 kD to 110 kD is the shortest at 35° C. (about 5 hours) and the longest at 15° C. (about 15 hours).

FIG. 3 shows an initial increase in polymer molecular weight. This phenomenon is most likely occurring because some portion of the polymer, particularly the lower molecular weight fractions is soluble in the extraction medium. Because the analytical measurement of molecular weight is a representation of all the molecular weight fractions present, removing (dissolving) the low molecular weight material can increase the measured molecular weight.

Methods of Preparing Microparticles

EXAMPLE 7

As exemplified by the examples discussed above, methods for preparing microparticles having a selected microparticle polymer molecular weight in accordance with the present invention will now be described in more detail. In one embodiment of the present invention, a first phase, comprising a nucleophilic compound, a polymer having a starting molecular weight, and a solvent for the polymer, is prepared. In one embodiment of the present invention, the first phase is prepared by dissolving a nucleophilic active agent in a first solvent to form an active agent solution. The polymer is dissolved in a second solvent to form a polymer solution. The active agent solution and the polymer solution are blended to form the first phase. In a particularly preferred embodiment, the active agent is selected from the group consisting of risperidone, 9–25 hydroxyrisperidone, and pharmaceutically acceptable salts thereof. In such an embodiment, a preferred first solvent is benzyl alcohol, and a preferred second solvent is ethyl acetate.

In another embodiment of the present invention, the first phase is prepared by dissolving the nucleophilic compound and the polymer in a solvent to form a solution. In yet a further embodiment, an active agent is added to the first phase. In a further embodiment, an inactive agent is added to the first phase. It should be understood that the present invention is not limited to any particular method or process by which the first phase is prepared, and other suitable processes would be readily apparent to one skilled in the art.

A second phase is prepared, and combined with the first phase under the influence of mixing means to form an emulsion. In a preferred embodiment, a static mixer is used to combine the two phases to form an emulsion. A process for forming an emulsion using a static mixer is described, for example, in U.S. Pat. No. 5,654,008, the entirety of which is incorporated herein by reference. The emulsion is combined with an extraction medium that extracts solvent from the emulsion droplets, thereby hardening them into microparticles.

Prior to combining the first and second phases, the first phase is maintained at a hold temperature for a hold period. The hold period is of sufficient duration to allow the starting molecular weight of the polymer to reduce to the selected microparticle polymer molecular weight at the hold temperature. Based on the teachings and examples provided herein, and the knowledge of skilled artisans, the determination of suitable hold temperatures and hold periods is within the routine skill of skilled artisans and would not require undue experimentation. In a preferred embodiment of the present invention, the starting molecular weight of the polymer reduces by about 10% to about 50% to reach the selected polymer molecular weight. However, it should be understood by one skilled in the art that the present invention is not limited to such a percentage reduction.

During the hold period, the first phase may be mixed, stirred, or otherwise agitated. Alternatively, during the hold period, the first phase may be subjected to no mixing, stirring, or agitation. The hold temperature is preferably in the range of from about 15° C. to about 35° C., more preferably about 25° C.

An alternate method for preparing microparticles in accordance with the present invention will now be described. A polymer having a starting molecular weight and a nucleophilic compound are dissolved in a solvent to form a first phase. An active agent and/or an inactive agent can be added to the first phase. The first phase is combined with a second phase under the influence of mixing means to form an emulsion. The emulsion is combined with an extraction medium that extracts solvent, thereby hardening the emulsion droplets into microparticles. Prior to combining the first and second phases, the first phase is maintained at a hold temperature for a hold period. The hold period is selected so that the starting molecular weight of the polymer reduces to a selected microparticle polymer molecular weight at the hold temperature. The duration of the hold period can be adjusted by changing the hold temperature in a manner as described above.

Microparticles of the Present Invention

The microparticles prepared by the process of the present invention preferably comprise a polymeric binder. Suitable polymeric binder materials include poly(glycolic acid), poly-d,l-lactic acid, poly-l-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and polyphosphazines. Poly (d,l-lactic-co-glycolic acid) is commercially available from Alkermes, Inc. (Blue Ash, Ohio). A suitable product commercially available from Alkermes, Inc. is a 50:50 poly(d,l-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL and poly(d,l-lactic acid) (100 DL). Poly(lactide-co-glycolides) are also commercially available from Boehringer Ingelheim (Germany) under its Resomer® mark, e.g., PLGA 50:50 (Resomer® RG 502), PLGA 75:25 (Resomer® RG 752) and d,l-PLA (Resomer® RG 206), and from Birmingham Polymers (Birmingham, Ala.). These copolymers are available in a wide range of molecular weights and ratios of lactic acid to glycolic acid.

One type of microparticle. suitable for preparation by the present invention is a sustained-release microparticle that is biodegradable. However, it should be understood by one skilled in the art that the present invention is not limited to biodegradable or other types of sustained-release microparticles. As would be apparent to one skilled in the art, the molecular weight of the polymeric binder material for biodegradable microparticles is of some importance. The molecular weight should be high enough to permit the formation of satisfactory polymer coatings, i.e., the polymer should be a good film former. However, since the properties of the film are also partially dependent on the particular polymeric binder material being used, it is very difficult to specify an appropriate molecular weight range for all polymers. The molecular weight of the polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric binder bioerodes. By an appropriate selection of polymeric materials a microparticle formulation can be made in which the resulting microparticles exhibit both diffusional release and biodegradation release properties. This is useful in according multiphasic release patterns. A satisfactory starting molecular weight of the polymer is in the range of 5–500 kD, preferably in the range of from about 50 kD to about 250 kD. The microparticle polymer molecular weight is preferably in the range of from about 10 kD to about 185 kD.

The microparticles prepared in accordance with the present invention may include an active agent or other type of substance that is released from the microparticles into the host. However, it should be understood that the present invention is not limited to preparation of microparticles that contain an active agent. The active agent can be a nucleophilic compound. Alternatively, the active agent is not a nucleophilic compound and is added to the microparticles during the formation process. Such active agents can include 1,2-benzazoles, more particularly, 3-piperidinyl-substituted 1,2-benzisoxazoles and 1,2-benzisothiazoles. The most preferred active agents of this kind are 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one ("risperidone") and 3-[2-[4-(6-fluro-1,2-benzisoxazol-3-yl)-1-piperidinyl] ethyl]-6,7,8,9-tetrahydro-9-hydroxy-2-methyl-4H-pyrido[1,2-a]pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Other biologically active agents include non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-Parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodienone, meperidine, morphine and the like; non-narcotics such as salicylates, aspirin, acetaminophen, d-propoxyphene and the like; opioid receptor antagonists, such as naltrexone and naloxone; antibiotics such as gentamycin, tetracycline and penicillins; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs.

Still other suitable active agents include estrogens, antibacterials; antifungals; antivirals; anticoagulants; anticonvulsants; antidepressants; antihistamines; and immunological agents.

Other examples of suitable biologically active agents include peptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antipyretic and analgesic agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and heparin; hemostatic agents such as thrombin, menadione sodium bisulfite and acetomenaphthone; antituberculous agents such as isoniazide and ethanbutol; hormones such as prednisolone sodium phosphate and methimazole.

The microparticles can be mixed by size or by type. However, it should be understood that the present invention is not limited to the use of biodegradable or other types of microparticles that contain an active agent. In one embodiment, the microparticles are mixed in a manner that provides for the delivery of active agent to the host in a multiphasic manner and/or in a manner that provides different active agents to the host at different times, or a mixture of active agents at the same time. For example, secondary antibiotics, vaccines, or any desired active agent, either in microparticle form or in conventional, unencapsulated form can be blended with a primary active agent and provided to the host.

Apparatus

Figure 4:
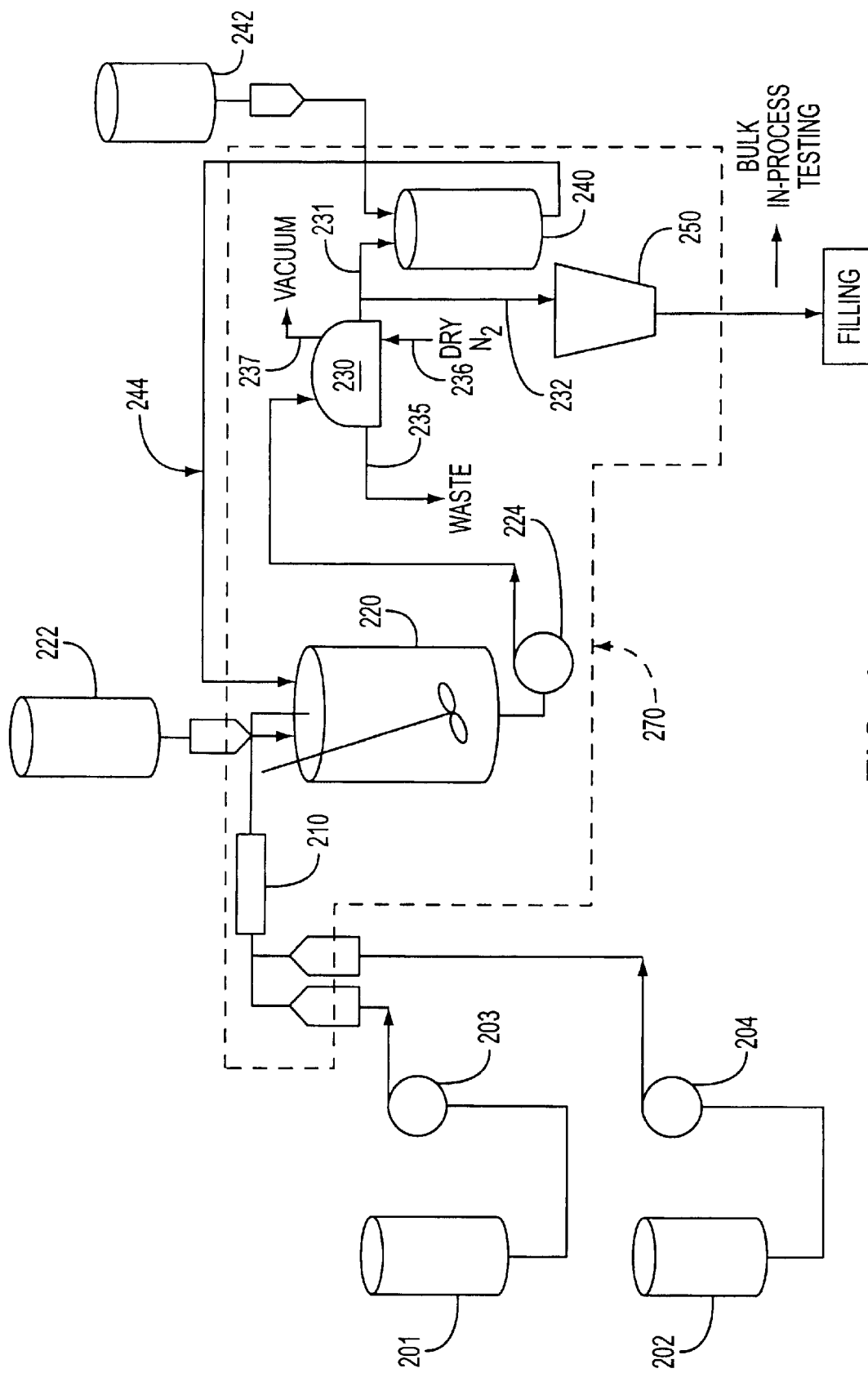
FIG. 4 shows one embodiment of an equipment configuration suitable for preparing microparticles in accordance with the present invention.

With reference now to FIG. 4, one embodiment is shown of an equipment configuration suitable for use in preparing microparticles in accordance with the present invention. In a preferred embodiment of the present invention, the equipment contained within the dotted line boundary shown generally at 270 is sterilized using a "steam-in-place" (SIP) process.

A first phase 201 is provided. First phase 201 is preferably the discontinuous phase, comprising a polymer dissolved in one or more solvents, and an active agent. The active agent can be dissolved or dispersed in the same or a different solvent than the solvent(s) in which the polymer is dissolved. A second phase 202 is preferably the continuous phase, preferably comprising water as the continuous processing medium. Preferably, an emulsifying agent such as a surfactant or a hydrophilic colloid is added to the continuous phase to prevent the microdroplets from agglomerating and to control the size of the microdroplets in the emulsion. Examples of compounds that can be used as surfactants or hydrophilic colloids include, but are not limited to, poly (vinyl alcohol) (PVA), carboxymethyl cellulose, gelatin, poly(vinyl pyrrolidone), Tween 80, Tween 20, and the like. The concentration of surfactant or hydrophilic colloid in the continuous phase will be from about 0.1% to about 10% by weight based on the continuous processing medium, depending upon the surfactant, hydrophilic colloid, the discontinuous phase, and the continuous processing medium used. A preferred continuous phase is 0.1 to 10 wt. %, more preferably 0.5 to 2 wt. %, solution of PVA in water. Although not absolutely necessary, it is preferred to saturate the continuous phase with at least one of the solvents forming the discontinuous phase.

First phase 201 and second phase 202 are combined under the influence of mixing means to form an emulsion. A preferred type of mixing means is a static mixer 210. Other mixing means suitable for use with the present invention include, but are not limited to, devices for mechanically agitating the first and second phases, such as homogenizers, propellers, impellers, stirrers, and the like.

Preferably, the discontinuous and continuous phases 201 and 202 are pumped through static mixer 210 to form an emulsion, and into a large volume of quench liquid, to obtain microparticles containing the active agent encapsulated in the polymeric matrix material. A pump 203 pumps first phase 201 into static mixer 210, and a pump 204 pumps second phase 202 into static mixer 210. An especially preferred method of mixing with a static mixer in the process of the present invention is disclosed in U.S. Pat. No. 5,654,008, the entirety of which is incorporated herein by reference.

First and second phases 201 and 202 are mixed in static mixer 210 to form an emulsion. The emulsion formed comprises microparticles containing active agent encapsulated in the polymeric matrix material. The microparticles are then preferably stirred in a quench or extraction tank 220 containing a quench liquid in order to remove most of the solvent from the microparticles, resulting in the formation of hardened microparticles. Following the movement of the microparticles from static mixer 210 and entrance into quench tank 220, the continuous processing medium is diluted, and much of the solvent in the microparticles is removed by extraction. In this extractive quench step, the microparticles can be suspended in the same continuous phase (second phase 202) used during emulsification, with or without hydrophilic colloid or surfactant, or in another quench liquid. The quench liquid removes a significant portion of the solvent from the microparticles, but does not dissolve them. During the extractive quench step, the quench liquid containing dissolved solvent can, optionally, be removed and replaced with fresh quench liquid.

Upon completion of the quench step in quench tank 220, the microparticles are transferred by a pump 224 to a device 230 that functions as a microparticle collecting device, de-watering device, and drying device.

Device 230 comprises a vibrating sieve or screen. The vibration causes smaller particles and liquid to drop through the screen, while larger particles are retained. The smaller particles and liquid that drop through the screen are removed as waste 235. Device 230 also functions as a vacuum dryer, through the use of a vacuum line 237. The microparticles are fluidized by the vibrational energy, and by a small amount of a dry gas bleed, preferably a dry nitrogen ($N_2$) bleed 236.

The dried microparticles are transferred to another extraction medium to carry out a wash step. The wash step is preferably carried out in quench tank 220, using an extraction medium 222 having a temperature higher than the glass transition temperature ($T_g$) of the microparticles. To carry out the wash step, the microparticles are first introduced into a re-slurry tank or other type of vessel 240, as shown by path 231. The temperature of the extraction medium 242 that is used in vessel 240 is lower than the $T_g$ of the microparticles.

After the wash step is completed in quench tank 220, the microparticles are again transferred via pump 224 into device 230 for de-watering and final drying. At the completion of final drying, the microparticles are discharged from device 230 in the manner described above into a sifter 250, as shown by path 232. Sifter 250 is used to fractionate the microparticles by size for filling into vials and for bulk in-process testing (e.g., aspect, active agent content, residual solvents, in vitro release, and particle size distribution).

Conclusion

While various embodiments of the present invention have been described above, it should be understood that they have been presented by way of example only, and not limitation. The present invention is not limited to the preparation of controlled release microparticles or microparticles containing an active agent, nor is it limited to a particular active agent, polymer or solvent, nor is the present invention limited to a particular scale or batch size. Thus, the breadth and scope of the present invention should not be limited by any of the above-described exemplary embodiments, but should be defined only in accordance with the following claims and their equivalents

What is claimed is:

1. A method of preparing microparticles having a selected microparticle polymer molecular weight, comprising:
    (a) preparing a first phase, the first phase comprising a nucleophilic compound, a polymer having a starting molecular weight, and a solvent for the polymer;
    (b) combining the first phase with a second phase under the influence of mixing means to form an emulsion;
    (c) combining the emulsion and an extraction medium, thereby forming microparticles; and
    (d) maintaining the first phase at a hold temperature for a hold period prior to step (b), the hold period of sufficient duration to allow the starting molecular weight of the polymer to reduce so that the selected microparticle polymer molecular weight is achieved.

2. The method of claim 1, further comprising:
    (e) increasing the hold temperature, thereby increasing molecular weight decay of the polymer to reduce a duration of the hold period.

3. The method of claim 1, further comprising:
    (e) decreasing the hold temperature, thereby decreasing molecular weight decay of the polymer to increase a duration of the hold period.

4. The method of claim 1, wherein the starting molecular weight is in the range of from about 50 kD to about 250 kD.

5. The method of claim 1, wherein the hold period is in the range of from about 0.05 hour to about 6 hours.

6. The method of claim 1, wherein the hold temperature is in the range of from about 15° C. to about 35° C.

7. The method of claim 1, wherein the mixing means is a static mixer.

8. The method of claim 1, wherein the nucleophilic compound is selected from the group consisting of risperidone, 9-hydroxyrisperidone, and pharmaceutically acceptable salts thereof.

9. The method of claim 8, wherein the solvent comprises benzyl alcohol and ethyl acetate.

10. The method of claim 1, wherein the polymer is selected from the group consisting of poly(glycolic acid), poly-d,l-lactic acid, poly-l-lactic acid, and copolymers of the foregoing.

11. The method of claim 10, wherein the polymer is poly(d,l-lactide-co-glycolide) having a molar ratio of lactide to glycolide in the range of from about 100:0 to about 50:50.

12. The method of claim 1, further comprising:
    (e) mixing the first phase during the hold period.

13. The method of claim 1, wherein the selected microparticle polymer molecular weight is in the range of from about 10 kD to about 185.0 kD.

14. The method of claim 4, wherein the selected microparticle polymer molecular weight is in the range of from about 10 kD to about 185.0 kD.

15. The method of claim 1, wherein the starting molecular weight reduces by an amount in the range of from about 10% to about 50% to reach the selected microparticle polymer molecular weight.

16. The method of claim 4, wherein the starting molecular weight reduces by an amount in the range of from about 10% to about 50% to reach the selected microparticle polymer molecular weight.

17. The method of claim 13, wherein the starting molecular weight reduces by an amount in the range of from about 10% to about 50% to reach the selected microparticle polymer molecular weight.

18. The method of claim 1, wherein the nucleophilic compound is an active agent.

19. The method of claim 1, wherein the nucleophilic compound is an inactive agent.

20. The method of claim 1, further comprising:
   (e) adding an active agent to the first phase.

21. The method of claim 1, further comprising:
   (e) adding an inactive agent to the first phase.

22. The method of claim 1, wherein the nucleophilic compound is basic.

23. The method of claim 1, wherein the nucleophilic compound is naltrexone.

24. The method of claim 1, wherein the nucleophilic compound is oxybutynin.

25. Microparticles having a selected microparticle polymer molecular weight prepared by the method of claim 1.

26. A method of preparing microparticles, comprising:
   (a) providing a polymer having a starting molecular weight;
   (b) dissolving the polymer and a nucleophilic compound in a solvent to form a first phase;
   (c) combining the first phase with a second phase under the influence of mixing means to form an emulsion;
   (d) combining the emulsion and an extraction medium, thereby forming microparticles; and
   (e) maintaining the first phase at a hold temperature for a hold period prior to step (c), wherein the hold period is selected so that the starting molecular weight reduces so that a selected microparticle polymer molecular weight is achieved.

27. The method of claim 26, further comprising:
   (f) increasing the hold temperature, thereby increasing molecular weight decay of the polymer to reduce a duration of the hold period.

28. The method of claim 26, further comprising:
   (f) decreasing the hold temperature, thereby decreasing molecular weight decay of the polymer to increase a duration of the hold period.

29. The method of claim 26, wherein the starting molecular weight is in the range of from about 50 kD to about 250 kD.

30. The method of claim 26, wherein the hold period is in the range of from about 0.05 hour to about 6 hours.

31. The method of claim 26, wherein the hold temperature is in the range of from about 15° C. to about 35° C.

32. The method of claim 26, wherein the mixing means is a static mixer.

33. The method of claim 26, further comprising:
   (f) adding an active agent to the first phase.

34. The method of claim 26, wherein the nucleophilic compound is selected from the group consisting of risperidone, 9-hydroxyrisperidone, and pharmaceutically acceptable salts thereof.

35. The method of claim 34, wherein the solvent comprises benzyl alcohol and ethyl acetate.

36. The method of claim 26, wherein the polymer is selected from the group consisting of poly(glycolic acid), poly-d,l-lactic acid, poly-l-lactic acid, and copolymers of the foregoing.

37. The method of claim 36, wherein the polymer is poly(d,l-lactide-co-glycolide) having a molar ratio of lactide to glycolide in the range of from about 100:0 to about 50:50.

38. The method of claim 26, further comprising:
   (f) mixing the first phase during the hold period.

39. The method of claim 26, wherein the selected microparticle polymer molecular weight is in the range of from about 10 kD to about 185.0 kD.

40. The method of claim 29, wherein the selected microparticle polymer molecular weight is in the range of from about 10 kD to about 185.0 kD.

41. The method of claim 29, wherein the starting molecular weight reduces by an amount in the range of from about 10% to about 50% to reach the selected microparticle polymer molecular weight.

42. The method of claim 26, wherein the starting molecular weight reduces by an amount in the range of from about 10% to about 50% to reach the selected microparticle polymer molecular weight.

43. The method of claim 39, wherein the starting molecular weight reduces by an amount in the range of from about 10% to about 50% to reach the selected microparticle polymer molecular weight.

44. The method of claim 26, wherein the nucleophilic compound is an active agent.

45. The method of claim 26, wherein the nucleophilic compound is an inactive agent.

46. The method of claim 26, further comprising:
   (f) adding an inactive agent to the first phase.

47. The method of claim 26, wherein the nucleophilic compound is basic.

48. The method of claim 26, wherein the nucleophilic compound is naltrexone.

49. The method of claim 26, wherein the nucleophilic compound is oxybutynin.

50. Microparticles prepared by the method of claim 26.

* * * * *

UNITED STATES PATENT AND TRADEMARK OFFICE
CERTIFICATE OF CORRECTION

PATENT NO. : 6,264,987 B1
DATED : July 24, 2001
INVENTOR(S) : Steven G. Wright et al.

It is certified that error appears in the above-identified patent and that said Letters Patent is hereby corrected as shown below:

Title page,
References Cited, include the following under U.S. PATENT DOCUMENTS:

| | | | |
|---|---|---|---|
| 3,523,906 | 08/1970 | Vrancken et al. | |
| 3,691,090 | 09/1972 | Kitajima et al. ..... | 252/316 |
| 3,737,337 | 06/1973 | Schnoring et al. ... | 117/100 |
| 3,773,919 | 11/1973 | Boswell et al. ...... | 424/19 |
| 3,891,570 | 06/1975 | Fukushima et al. ... | 252/316 |
| 3,960,757 | 06/1976 | Morishita et al. ..... | 252/316 |
| 4,221,862 | 09/1980 | Naito et al. .......... | 430/536 |
| 4,384,975 | 05/1983 | Fong.................. | 427/213.36 |
| 4,389,330 | 06/1983 | Tice et al. ............ | 427/213.36 |
| 4,530,840 | 07/1985 | Tice et al. ............ | 514/179 |
| 4,818,517 | 04/1989 | Kwee et al. ........... | 424/488 |
| 4,940,588 | 07/1990 | Sparks et al. .......... | 424/490 |
| 5,066,436 | 11/1991 | Komen et al. .......... | 264/4.3 |
| 5,407,609 | 04/1995 | Tice et al. ............. | 264/46 |
| 5,428,024 | 06/1995 | Chu et al. .............. | 514/021 |
| 5,478,564 | 12/1995 | Wantier et al. ......... | 424/426 |
| 5,541,172 | 07/1996 | Labric et al. ........... | 514/169 |
| 5,650,173 | 07/1997 | Ramstack et al. ....... | 424/489 |
| 5,654,010 | 08/1997 | Johnson et al. ......... | 424/502 |
| 5,656,297 | 08/1997 | Bernstein et al. ........ | 424/484 |
| 5,656,299 | 08/1997 | Kino et al. ............. | 424/489 |
| 5,658,593 | 08/1997 | Orly et al. .............. | 424/499 |
| 5,667,808 | 09/1997 | Johnson et al. ......... | 424/501 |
| 5,688,801 | 11/1997 | Mesens et al. .......... | 514/258 |
| 5,770,231 | 06/1998 | Mesens et al. .......... | 424/497 |
| 5,747,058 | 05/1998 | Tipton et al. ........... | 424/423 |
| 5,792,477 | 08/1998 | Rickey et al. ........... | 424/501 |
| 5,871,778 | 02/1999 | Kino et al. ............. | 424/489 |
| 5,916,598 | 06/1999 | Rickey et al. ........... | 424/501 |
| 5,942,253 | 08/1999 | Gombotz et al. ........ | 424/501 |
| 5,965,168 | 10/1999 | Mesens et al. .......... | 424/497 |

UNITED STATES PATENT AND TRADEMARK OFFICE
CERTIFICATE OF CORRECTION

PATENT NO. : 6,264,987 B1
DATED : July 24, 2001
INVENTOR(S) : Steven G. Wright et al.

It is certified that error appears in the above-identified patent and that said Letters Patent is hereby corrected as shown below:

References Cited, include the following under FOREIGN PATENT DOCUMENTS:

| | | |
|---|---|---|
| 0 486 959 | 05/1992 | European Patent Office |
| 0 831 773 | 12/1999 | European Patent Office |
| WO 89/03678 | 05/1989 | WIPO |
| WO 90/13361 | 11/1990 | WIPO |
| WO 94/10982 | 05/1994 | WIPO |
| WO 95/13799 | 05/1995 | WIPO |
| WO 96/40049 | 12/1996 | WIPO |
| WO 97/41837 | 11/1997 | WIPO |
| WO 99/12549 | 03/1999 | WIPO |

References Cited, include the following under OTHER DOCUMENTS:
Beck, L.R., Biology of Reproduction, 28: 186-195 (February 1983).
Bodmeier, R., et al., International Journal of Pharmaceutics, 43:179-186 (1988).
Cha, Y., et al., Journal of Controlled Release, 8:259-265 (1989).
Cha, Y., et al., Journal of Controlled Release, 7:69-78 (1988).
Jalil, R. et al., Journal of Microencapsulation, Volume 7, Number 3, pp. 297-319, July-September 1990.
Li, Wen-I et al., Journal of Controlled Release, 37:199-214 (December 1995).
Maulding, H.V. et al., Journal of Controlled Release, 3:103-117 (March 1986).
Sah, Hongkee et al., Pharmaceutical Research, 13:360-367 (March 1996).
Sato, Toyomi et al., Pharmaceutical Research, 5:21-30 (1988).

Signed and Sealed this

Thirtieth Day of April, 2002

*Attest:*

JAMES E. ROGAN
*Attesting Officer*     *Director of the United States Patent and Trademark Office*